(12) United States Patent
Wu et al.

(10) Patent No.: US 12,390,166 B2
(45) Date of Patent: Aug. 19, 2025

(54) INTRAVASCULAR DOPPLER BLOOD FLOW MEASUREMENT FROM INTRAVASCULAR GUIDEWIRE FOR BLOOD VESSEL ASSESSMENT

(71) Applicant: PHILIPS IMAGE GUIDED THERAPY CORPORATION, San Diego, CA (US)

(72) Inventors: Hoi San Wu, Eindhoven (NL); Ronald Christiaan Helmstrijd, Eindhoven (NL); Reinoud Bosman, Eindhoven (NL); Martijn Anne Van Lavieren, Abcoude (NL); David Michael Anderson, Temecula, CA (US); Arjen Van Der Horst, Tilburg (NL); Duy Le, Eindhoven (NL); Chantal Nathalie Van Den Broek, Schijndel (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 227 days.

(21) Appl. No.: 18/095,558

(22) Filed: Jan. 11, 2023

(65) Prior Publication Data
US 2023/0218230 A1 Jul. 13, 2023

Related U.S. Application Data

(60) Provisional application No. 63/298,717, filed on Jan. 12, 2022.

(51) Int. Cl.
*A61B 5/00* (2006.01)
*A61B 8/00* (2006.01)

(52) U.S. Cl.
CPC ............ *A61B 5/6852* (2013.01); *A61B 5/743* (2013.01); *A61B 8/488* (2013.01); *A61M 2205/3334* (2013.01)

(58) Field of Classification Search
None
See application file for complete search history.

(56) References Cited

U.S. PATENT DOCUMENTS

| | | |
|---|---|---|
| 2015/0305679 A1 | 10/2015 | Matsubara |
| 2020/0129148 A1 | 4/2020 | Jenkins |

FOREIGN PATENT DOCUMENTS

| | | |
|---|---|---|
| EP | 3854310 A1 | 7/2021 |
| WO | 2020148162 A1 | 7/2020 |

*Primary Examiner* — Boniface N Nganga

(57) ABSTRACT

An intravascular blood flow sensing system is provided. The system includes an intravascular catheter or guidewire with a flow sensor that obtains flow data of blood flow within a blood vessel. The system includes a processor circuit that communicates with the intravascular catheter or guidewire. The processor circuit receives the flow data from the intravascular catheter or guidewire, determine a plurality of values based on the flow data, and outputs a plot of the plurality of values to a display. The plot includes peak associated with coronary reactivity testing (CRT). The processor circuit can also automatically change between a louder volume and a softer volume for audio output of the flow data. The processor circuit can additional communicate with a device other than the flow sensor (e.g., ECG, pressure sensor, etc.), and graphical representations of the flow data and the data received from the other device can be independent scaled.

10 Claims, 15 Drawing Sheets

INTRAVASCULAR DOPPLER BLOOD FLOW MEASUREMENT FROM INTRAVASCULAR GUIDEWIRE FOR BLOOD VESSEL ASSESSMENT

TECHNICAL FIELD

The subject matter described herein relates to devices and methods for supporting the diagnosis of intravascular disease. For example, aspects of the present application are related to intravascular Doppler blood flow measurement from an intravascular guidewire and/or other medical data for assessment of a patient's blood vessel.

BACKGROUND

Cardiovascular disease is among the world's leading causes of death. To address this problem, physicians make use of a wide variety of data gathering modalities as well as in-body diagnostic devices, e.g., sensing guidewires and catheters. These catheters and guidewires may be inserted into a patient's vasculature for the purpose of assessing the conditions within the patient's blood vessels.

Flow reserve is a concept that estimates the extent flow can increase over a resting baseline. Fractional Flow Reserve (FFR) and instant wave-Free Ratio (iFR) are indices that rely on pressure as a substitute for flow in estimating the competency of a coronary epicardial artery. FFR and iFR are currently used as the go-to standard to identify candidates for percutaneous coronary intervention (PCI). A significant percentage of the population with microvascular coronary artery disease (CAD), predominantly women, does not qualify as a PCI candidate using pressure-based measurements because their disease is primarily located in the coronary microvasculature, rather than in the large coronary vessels.

Coronary Flow Reserve (CFR) uses velocity as the basis of its measurement. CFR is an index that covers both epicardial and microvascular arterial domains. Additionally, other indices, e.g., Microvascular Resistance Index (MRI), Hyperemic Microvascular Resistance (HMR), and Index of Microcirculatory Resistance (IMR), measure only the microvascular contribution to CAD. These indices rely on direct measurement of flow.

Coronary Reactivity Testing (CRT) is another assessment a physician may perform to help locate blockages that may be present. In CRT, the physician observes how blood vessels react to a vasoactive agent, e.g., by looking for spasms or other activity in the vessels. CRT can be especially useful in helping to diagnose microvascular dysfunction.

The information included in this Background section of the specification, including any references cited herein and any description or discussion thereof, is included for technical reference purposes only and is not to be regarded as subject matter by which the scope of the disclosure is to be bound.

SUMMARY

A sensing guidewire can be used, for example, to gather data to be used in the assessment of Non-Obstructive Coronary Artery Disease (NOCAD) and MicroVascular Disease (MVD). The present disclosure adds novel capabilities to vascular assessment systems, including techniques to improve assessment accuracy and reduce the occurrence of repeat assessments. In some cases, assessment data from multiple data gathering modalities may be presented on a display. The assessment data may be navigable and adjustable by a user of the vascular assessment system.

Such techniques may be useful in blood flow measurements, Doppler ultrasound measurements, blood pressure measurements, and electrocardiogram (ECG) measurements, as well as in other cardiovascular assessments. The assessment systems, devices, and methods described herein have particular, but not exclusive, utility in the context of a catheterization laboratory. The present disclosure advantageously provides devices, systems, and methods to simplify the gathering and interpretation of data regarding the state of a patient's vasculature, which address the dangers of cardiovascular disease.

In an exemplary aspect, an intravascular blood flow sensing system is provided. The system includes an intravascular catheter or guidewire comprising a flow sensor configured to obtain flow data of blood flow within a blood vessel; a display; and a processor circuit configured for communication with the display and the intravascular catheter or guidewire, wherein the processor circuit is configured to: receive the flow data from the intravascular catheter or guidewire; determine, based on the flow data, a plurality of values associated with coronary reactivity testing (CRT); and output, to the display, a plot of the plurality of values such that the plot is representative of a progress of the CRT.

In some aspects, the plurality of values comprises a plurality of average peak velocity (APV) values. In some aspects, the processor is configured to: output, to the display, a locator overlaid on the plot; and receive a user input moving the locator along the plot. In some aspects, the processor configured to output, to the display, a first graphical representation of the flow data associated with a first position of the locator along the plot. In some aspects, the plot of the average values comprises a baseline, the processor is configured to output a second graphical representation of the flow data associated with a second position of the baseline along the plot, and the first graphical representation and the second graphical representation are displayed simultaneously. In some aspects, the processor is configured to output, to the display, a bookmark along the plot. In some aspects, the processor is configured to automatically generate the bookmark. In some aspects, the processor is configured to determine a position for the bookmark along the plot based on a shape of the plot. In some aspects, the bookmark identifies a peak of the plot. In some aspects, the plot of values comprises a plurality of peaks, the processor is configured to output, to the display, a list of the plurality of peaks, and the processor is configured to receive a user input identifying a peak of the plurality of peaks in the list, and the processor is configured to output a graphical representation of the flow data associated with identified peak.

In an exemplary aspect, an intravascular blood flow sensing system is provided. The system includes an intravascular catheter or guidewire comprising a flow sensor configured to obtain flow data associated with blood flow within a blood vessel; an audio output device configured to output sound associated with the flow data; and a processor circuit configured for communication with the audio output device and the intravascular catheter or guidewire, wherein the processor circuit is configured to: receive first flow data from the intravascular catheter or guidewire, wherein the first flow data is obtained while the flow sensor is positioned at a data collection location within the blood vessel; receive second flow data from the intravascular catheter or guidewire, wherein the second flow data is obtained while at least one of: the intravascular catheter or guidewire is being moved to position the flow sensor at the data collection location; or the first flow data is under review by a user; output, via the audio output device, the sound associated with the first flow data at a first volume; and output, via the audio output device, the sound associated with the second flow data at a second volume that is less than the first volume, wherein the processor circuit is configured to automatically change the sound between the first volume and the second volume.

In some aspects, the processor circuit is further configured to determine when the first flow data or the second flow data is being received based on a user input and thereafter automatically change the sound between the first volume and the second volume. In some aspects, wherein the user input comprises recording of the first flow data, and, when the user input comprises recording of the first flow data, the processor circuit is configured to change the sound to the first volume. In some aspects, the user input comprises the review by the user of the first flow data, when the user input comprises the review by the user of the first flow data, the processor circuit is configured to change the sound to the second volume. In some aspects, the processor circuit is further configured to determine when the first flow data or the second flow data is being received based on a waveform of the first flow data or the second flow data, and thereafter automatically change the sound between the first volume and the second volume.

In an exemplary aspect, a system for evaluating a blood vessel of a patient is provided. The system includes an intravascular flow sensing guidewire configured to obtain blood flow data from the blood vessel while the intravascular flow sensing guidewire is positioned within the blood vessel; and a processor circuit configured for communication with the intravascular flow sensing guidewire and a further device, wherein the processor circuit is configured to: receive the blood flow data from the intravascular flow sensing guidewire, receive data from the further device, output, on a display in communication with the processor circuit, a graphical representation of the blood flow data and a graphical representation of the data received from the further device, wherein the graphical representations are independently scaled on respective y-axes.

In an exemplary aspect, a system for evaluating a blood vessel of a patient is provided. The system includes a processor circuit configured for communication with a first device and a second device, wherein the processor circuit is configured to: receive first modality data from the first device, the first device comprising an intravascular flow sensor, wherein the first modality data is blood flow data gathered within the blood vessel; receive second modality data from the second device; and output, on a display in communication with the processor circuit, a first graphical representation of the first modality data and a second graphical representation of the second modality data, wherein the first and second graphical representations are independently scaled on respective y-axes.

In some aspects, the processor circuit is further configured to output, on the display, one or more workflow suggestions. In some aspects, the second modality data is electrocardiogram (ECG) data. In some aspects, the processor circuit is further configured to output, on the display, a polar plot comprising a plurality of regions, wherein the number of regions in the polar plot corresponds to the number of ECG leads attached to the patient, and wherein the color of each respective region indicates the presence or absence of a detected condition in that region. In some aspects, the processor circuit is further configured to scale the first and second graphical representations automatically. In some aspects, the processor circuit is further configured to output, on the display adjacent to the first and second graphical representations, numerical representations of a plurality of clinical parameters calculated from data obtained using at least one of the first modality, the second modality, or a third modality. In some aspects, the processor circuit is further configured to output, on the display, an interactive trendline representative of at least one of the first graphical representation or the second graphical representation averaged over time. In some aspects, the processor circuit is further configured to: detect a triggering event; automatically generate an event bookmark marking a location of interest on the interactive trendline in response to the triggering event; and output, on the display, the event bookmark. In some aspects, the processor circuit is further configured to update the event bookmark in response to input from a user. In some aspects, the user input specifies a set of heartbeats to be included in the event bookmark. In some aspects, the set of heartbeats includes at least one discontinuity. In some aspects, the processor circuit is further configured to: receive imaging data from an imaging device external to the patient; synchronize the imaging data with at least one of the first modality data or the second modality data; generate an anatomic image based on the imaging data; and output the anatomic image on the display. In some aspects, the processor circuit is further configured to automatically adjust the volume of a procedure that uses at least one of the first modality or the second modality. In some aspects, the processor circuit is further configured to adjust a tracing of at least one of the first graphical representation or the second graphical representation based on user input. In some aspects, the processor circuit is further configured to output, on the display, a list of one or more previously calculated clinical parameters. In some aspects, the processor circuit is further configured to allow a user to navigate previously recorded data while the processor circuit obtains and outputs, on the display, live data.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the disclosed devices, systems, and methods, as defined in the claims, is provided in the following written description of various embodiments of the disclosure and is illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
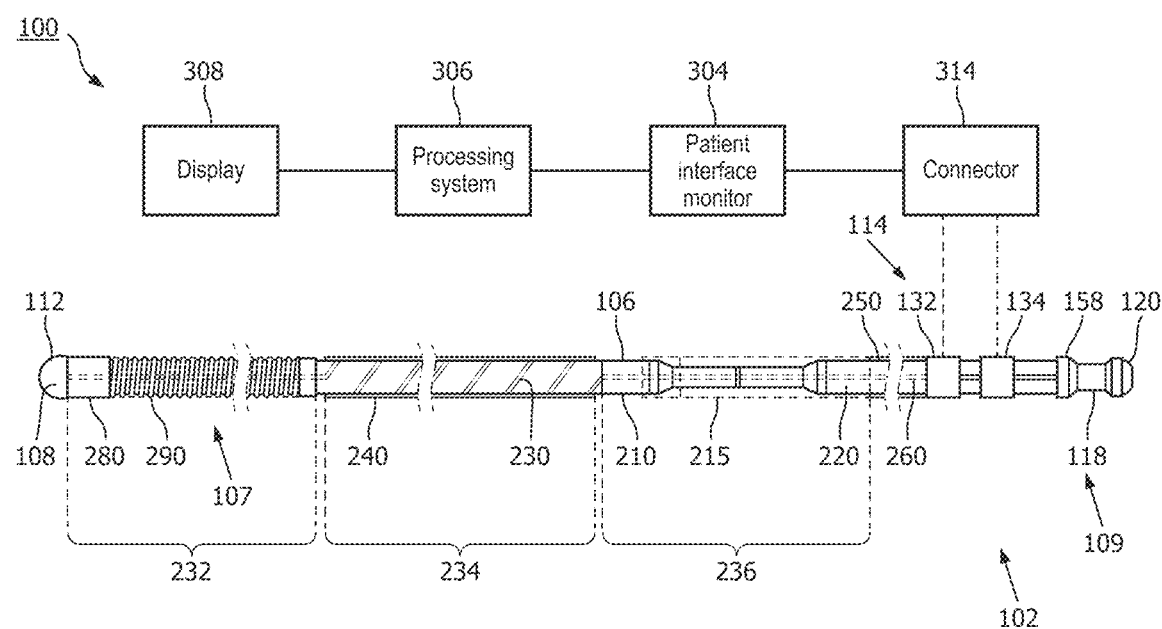
FIG. 1 is a diagrammatic side view of an intravascular sensing system that includes an intravascular device, according to aspects of the present disclosure.

Coronary artery disease (CAD) is among the world's leading causes of death. To address this problem, Philips Image Guided Therapy (IGT) has a strong portfolio in imaging systems (for e.g. coronary angiography) as well as in-body diagnostic devices (e.g. pressure-sensing guidewires or intravascular ultrasound catheters). One such diagnostic device is the blood flow velocity sensing guidewire, which can be used for example to assess Non-Obstructive Coronary Artery Disease (NOCAD) and Micro-Vascular Disease (MVD). These guidewires are equipped with a single-element ultrasound transducer that is located at its tip. The transducer can emit ultrasound waves in a forward-looking direction and receive the corresponding pulse-echo signals. By pulsed-wave (PW) Doppler analysis, the blood velocity distribution in a specific sampling volume can be deduced.

Clinical outcomes of interventions may be improved when they are based on translesional physiology measurements. Rather than relying on angiography, modern coronary assessment may rely on physiology and the measurement of flow. Historically, flow measurements preceded pressure-based measurements for coronary assessment. However, clinically, it was sometimes more efficient to substitute pressure for flow. The downside of this substitution is the omission of the microvascular contribution in the coronary assessment. While it has been demonstrated that epicardial measurements (FFR, iFR) increased the reliance on physiology, it has been further demonstrated that epicardial measurements may not give the whole picture. When interpreting the diagnostic characteristics of FFR, it can be important to acknowledge FFR is derived as a surrogate measure of coronary flow impairment and is not the same as direct measurements of coronary flow, which may be critical determinants of conditions such as myocardial ischemia.

Flow measurements can be acquired using thermodilution, but there is speculation that the accuracy of the thermodilution method may be compromised in pulsatile flow. The concept of flow measurement has been demonstrated to provide significant understanding to the assessment of coronary stenosis and the application of FFR.

The present disclosure provides techniques that improve flow assessment. The outputs of the methods disclosed herein may be viewable on a display, and the methods may be operated by a control process executing on a processor that accepts user inputs from a keyboard, mouse, or touch-screen interface, and that is in communication with one or more sensors. In that regard, the control process performs certain specific operations in response to different inputs or selections made at different times. Certain structures, functions, and operations of the processor, display, sensors, and user input systems are known in the art, while others are recited herein to enable novel features or aspects of the present disclosure with particularity.

These descriptions are provided for exemplary purposes only and should not be considered to limit the scope of the disclosure. Certain features may be added, removed, or modified without departing from the spirit of the claimed subject matter. In particular, it is expressly contemplated that aspects of different embodiments may be implemented together, including in ways other than what is specifically described herein.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. Additionally, while the description below may refer to blood vessels, it will be understood that the present disclosure is not limited to such applications. For example, the devices, systems, and methods described herein may be used in any body chamber or body lumen, including an esophagus, veins, arteries, intestines, ventricles, atria, or any other body lumen and/or chamber. For the sake of brevity, however, the numerous iterations of these combinations will not be described separately.

FIG. 1 is a diagrammatic side view of an intravascular sensing system 100 that includes an intravascular device 102 according to aspects of the present disclosure. The intravascular device 102 can be an intravascular guidewire sized and shaped for positioning within a vessel of a patient. The intravascular device 102 can include a distal tip 108 and a sensing component 112. The sensing component 112 can be an electronic, electromechanical, mechanical, optical, and/or other suitable type of sensor. For example, the sensing component 112 can be a flow sensor configured to measure the velocity of blood flow within a blood vessel of a patient, a pressure sensor configured to measure a pressure of blood flowing within the vessel, or another type of sensor including but not limited to a temperature or imaging sensor. In some cases, the intravascular device 102 may comprise multiple sensing components 112. In such cases, the sensing components 112 may be different and may be disposed at different locations along the intravascular device 102. For example, a first sensing component 112 may be a flow sensor disposed at the distal tip 108 and a second sensing component 112 may be a pressure sensor disposed proximal to the distal tip 108. Flow data obtained by a flow sensor can be used to calculate physiological variables such as coronary flow reserve (CFR). Pressure data obtained by a pressure sensor may for example be used to calculate a physiological pressure ratio (e.g., FFR, iFR, Pd/Pa, or any other suitable pressure ratio). Flow and pressure data can be used together to calculate other diagnostic indices or to measure dynamic responses such as pressure-volume loops (P-V loops). An imaging sensor may include an intravascular ultrasound (IVUS), intracardiac echocardiography (ICE), optical coherence tomography (OCT), or intravascular photoacoustic (IVPA) imaging sensor. For example, the imaging sensor can include one or more ultrasound transducer elements, including an array of ultrasound transducer elements.

The intravascular device 102 includes a flexible elongate member 106. The sensing component 112 is disposed at the distal portion 107 of the flexible elongate member 106. The sensing component 112 can be mounted at the distal portion 107 within a housing 280 in some embodiments. A flexible tip coil 290 extends distally from the housing 280 at the distal portion 107 of the flexible elongate member 106. A connection portion 114 located at a proximal end of the flexible elongate member 106 includes conductive portions 132, 134. In some embodiments, the conductive portions 132, 134 can be conductive ink that is printed and/or deposited around the connection portion 114 of the flexible elongate member 106. In some embodiments, the conductive portions 132, 134 are conductive, metallic rings that are positioned around the flexible elongate member. A locking section is formed by collar 118 and knob 120 are disposed at the proximal portion 109 of the flexible elongate member 106.

The intravascular device 102 in FIG. 1 includes a distal core 210 and a proximal core 220. The distal core 210 and the proximal core 220 are metallic components forming part of the body of the intravascular device 102. For example, the distal core 210 and the proximal core 220 are flexible metallic rods that provide structure for the flexible elongate member 106. The diameter of the distal core 210 and the proximal core 220 can vary along its length. A joint between the distal core 210 and proximal core 220 may be surrounded and contained by a hypotube 215.

In some embodiments, the intravascular device 102 comprises a distal assembly and a proximal assembly that are electrically and mechanically joined together, which provides for electrical communication between the sensing component 112 and the conductive portions 132, 134. For example, flow data obtained by the sensing component 112 (in this example, sensing component 112 is a flow sensor) can be transmitted to the conductive portions 132, 134. Control signals (e.g., operating voltage, start/stop commands, etc.) from a processing system 306 in communication with the intravascular device 102 can be transmitted to the sensing component 112 via a connector 314 that is attached to the conductive portions 132, 134. In some embodiments, connector 314 may be replaced with a wireless connection. The wireless connection may be accomplished using any suitable wireless communication technology, including but not limited to one or more of: Bluetooth, Wi-Fi, ZigBee, Li-Fi, or cellular data connections such as 2G/GSM, 3G/UMTS, 4G/LTE/WiMax, or 5G. The distal subassembly can include the distal core 210. The distal subassembly can also include the sensing component 112, a conductor bundle 230, and/or one or more layers of insulative polymer/plastic 240 surrounding the conductive members 230 and the core 210. For example, the polymer/plastic layer(s) can insulate and protect the conductive members of the multi-filar cable or conductor bundle 230. The proximal subassembly can include the proximal core 220. The proximal subassembly can also include one or more layers of polymer layer(s) 250 (hereinafter polymer layer 250) surrounding the proximal core 220 and/or conductive ribbons 260 embedded within the one or more insulative and/or protective polymer layer(s) 250. In some embodiments, the proximal subassembly and the distal subassembly can be separately manufactured. During the assembly process for the intravascular device 102, the proximal subassembly and the distal subassembly can be electrically and mechanically joined together. As used herein, flexible elongate member can refer to one or more components along the entire length of the intravascular device 102, one or more components of the proximal subassembly (e.g., including the proximal core 220, etc.), and/or one or more components the distal subassembly 210 (e.g., including the distal core 210, etc.). The joint between the proximal core 220 and distal core 210 is surrounded by the hypotube 215.

In various embodiments, the intravascular device 102 can include one, two, three, or more core wires extending along its length. For example, in one embodiment, a single core wire extends substantially along the entire length of the flexible elongate member 106. In such embodiments, a locking section 118 and a section 120 can be integrally formed at the proximal portion of the single core wire. The sensing component 112 can be secured at the distal portion of the single core wire. In other embodiments, such as the embodiment illustrated in FIG. 1, the locking section 118 and the section 120 can be integrally formed at the proximal portion of the proximal core 220. The sensing component 112 can be secured at the distal portion of the distal core 210. 109

As described herein, electrical communication between the conductive members 230 and the conductive ribbons 260 can be established at the connection portion 114 of the flexible elongate member 106. By establishing electrical communication between the conductor bundle 230 and the conductive ribbons 260, the conductive portions 132, 134 can be in electrically communication with the sensing component 112.

In some embodiments represented by FIG. 1, intravascular device 102 includes a locking section 118 and a section 120. To form locking section 118, a machining process is necessary to remove polymer layer 250 and conductive ribbons 260 in locking section 118 and to shape proximal core 220 in locking section 118 to the desired shape. As shown in FIG. 1, locking section 118 includes a reduced diameter while section 120 has a diameter substantially similar to that of proximal core 220 in the connection portion 114. In some instances, because the machining process removes conductive ribbons in locking section 118, proximal ends of the conductive ribbons 260 would be exposed to moisture and/or liquids, such as blood, saline solutions, disinfectants, and/or enzyme cleaner solutions, an insulation layer 158 is formed over the proximal end portion of the connection portion 114 to insulate the exposed conductive ribbons.

In some embodiments, a connector 314 provides electrical connectivity between the conductive portions 132, 134 and a patient interface module or patient interface monitor 304. The patient interface module (PIM) 304 may in some cases connect to a console or processing system 306, which includes or is in communication with a display 308. In some embodiments, the patient interface module 304 includes signal processing circuitry, such as an analog-to-digital converter (ADC), analog and/or digital filters, signal conditioning circuitry, and any other suitable signal processing circuitry for processing the signals provided by the sensing component 112 for use by the processing system 306.

The system 100 may be deployed in a catheterization laboratory having a control room. The processing system 306 may be located in the control room. Optionally, the processing system 306 may be located elsewhere, such as in the catheterization laboratory itself. The catheterization laboratory may include a sterile field while its associated control room may or may not be sterile depending on the procedure to be performed and/or on the health care facility. In some embodiments, intravascular device 102 may be controlled from a remote location such as the control room, such than an operator is not required to be in close proximity to the patient.

The intravascular device 102, PIM 304, and display 308 may be communicatively coupled directly or indirectly to the processing system 306. These elements may be communicatively coupled to the processing system 306 via a wired connection such as via conductor bundle 230. The processing system 306 may be communicatively coupled to one or more data networks, e.g., a TCP/IP-based local area network (LAN). In other embodiments, different protocols may be utilized such as Synchronous Optical Networking (SONET). In some cases, the processing system 306 may be communicatively coupled to a wide area network (WAN).

The PIM 304 transfers the received signals to the processing system 306 where the information is processed and displayed on the display 308. The console or processing system 306 can include a processor and a memory. The processing system 306 may be operable to facilitate the features of the intravascular sensing system 100 described herein. For example, the processor can execute computer readable instructions stored on the non-transitory tangible computer readable medium.

The PIM 304 facilitates communication of signals between the processing system 306 and the intraluminal device 102. In some embodiments, the PIM 304 performs preliminary processing of data prior to relaying the data to the processing system 306. In examples of such embodiments, the PIM 304 performs amplification, filtering, and/or aggregating of the data. In an embodiment, the PIM 304 also supplies high- and low-voltage DC power to support operation of the intraluminal device 102 via the multi-filar conductor bundle 230.

The display or monitor 308 may be a display device such as a computer monitor, a touch-screen display, a television screen, or any other suitable type of display. The monitor 308 may be used to display selectable prompts, instructions, and visualizations of imaging data to a user. In some embodiments, the monitor 308 may be used to provide a procedure-specific workflow to a user to complete an intraluminal imaging procedure.

Before continuing, it should be noted that the examples described above are provided for purposes of illustration and are not intended to be limiting. Other devices and/or device configurations may be utilized to carry out the operations described herein.

Figure 2:
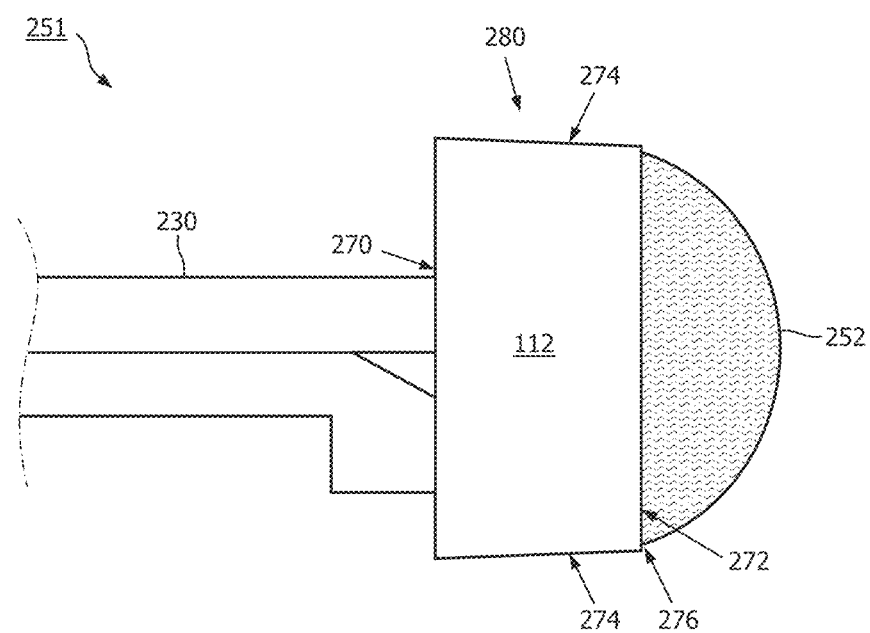
FIG. 2 is side cross sectional view of an example electronic component of an intravascular device, in accordance with aspects of the present disclosure.

FIG. 2 is a diagrammatic cross-sectional view of an example sensor assembly 251, which may for example be included in the intravascular device 102 of FIG. 1. More specifically, FIG. 2 illustrates a sensor assembly 251 that includes sensing component 112, housing 280, and an acoustic matching layer 252. As indicated by the positions of the sensing component 112 and the housing 280 illustrated in FIG. 1, the sensor assembly 251 may be included in a distal portion of the intravascular device 102 such that the surface 272 of the sensing component 112 faces distally.

As illustrated in FIG. 2, the sensing component 112 is positioned within the housing 280 and includes a proximal surface 270, an opposite, distal surface 272, and a side surface 274. In some embodiments, one or more of the proximal surface 270, the distal surface 272, or the side surface 274 may be coated in an insulating layer 276. The insulating layer 276 may be formed from parylene, which may be deposited on the one or more surfaces, for example. The insulating layer 276 may additionally or alternatively be formed from any other suitable insulating material. In some embodiments, the insulating layer 276 may prevent a short (e.g., an electrical failure), which may otherwise be caused by contact between a conductive portion of the sensing component 112 and the housing 280, which may be formed with a metal. As used herein, references to the distal surface 272 encompass the insulating layer 276 in embodiments where a distal end of the sensing component 112 is covered by the insulating layer 276, references to the proximal surface 270 encompass the insulating layer in embodiments where a proximal end of the sensing component 112 is covered by the insulating layer 276, and references to the side surface 274 encompass the insulating layer in embodiments where the side of the sensing component 112 is covered by the insulating layer 276 unless indicated otherwise.

In some embodiments, the sensing component 112 may include a transducer element, such as an ultrasound transducer element on the distal surface 272 such that the transducer element faces distally and may be used by the sensing component 112 to obtain sensor data corresponding to a structure distal of the sensing component 112. The sensing component 112 may additionally or alternatively include a transducer element on the proximal surface 270 such that the transducer faces proximally and may be used to obtain sensor data corresponding to a structure proximal of the sensing component. A transducer element may additionally or alternatively be positioned on a side surface 274 (e.g., on a perimeter or circumference) of the sensing component 112 in some embodiments.

As further illustrated, the sensing component 112 is coupled to the conductor bundle 230, and at least a portion (e.g., a distal portion) of the conductor bundle 230 extends through the housing 280. In particular, conductor bundle 230 may couple to an element, such as a transducer (e.g., an ultrasound transducer), of the sensing component 112 and may provide power, control signals, an electrical ground or signal return, and/or the like to the element. As described above, such an element may be positioned on the distal surface 272 of the sensor.

In some embodiments, the acoustic matching layer 252 may be positioned on (e.g., over) the distal surface 272 of the sensing component 112. In particular, the acoustic matching layer 252 may be disposed directly on the sensing component 112, or the acoustic matching layer 252 may be disposed on the insulating layer 276 coating the sensing component 112. Further, the acoustic matching layer 252 may be disposed on a transducer element (e.g., an ultrasound transducer element) positioned on the sensing component (e.g., the distal surface 272) and/or at least a portion of the conductor bundle 230 that is in communication with the transducer element. Moreover, the acoustic matching layer 252 may provide acoustic matching to the sensing component 112 (e.g., to an ultrasound transducer of the sensing component 112). For instance, the acoustic matching layer 252 may minimize acoustic impedance mismatch between the ultrasound transducer and a sensed medium, such as a fluid and/or a lumen that the intravascular device 102 is positioned within. In that regard, the acoustic matching layer 252 may be formed from any suitable material, such as a polymer or an adhesive, to provide acoustic matching with the sensing component 112. The portion of the acoustic matching layer 252 positioned on the distal surface 272 may include and/or be formed from the same material as a portion of the acoustic matching layer positioned on the side surface 274 and/or the proximal surface 270. Further, the acoustic matching layer 252 may be applied to the sensing component 112 before or after the sensing component 112 is positioned within the housing 280 during assembly of the sensor assembly 250. In this regard, the portion of the acoustic matching layer 252 positioned on the distal surface 272 and the portion of the acoustic matching layer positioned on the side surface 274 and/or the proximal surface 270 may be included in the sensor assembly 251 in the same or different steps. Further, in addition to the one or more materials the acoustic matching layer 252 is formed from, the acoustic matching layer 252 may provide acoustic matching with the sensing component 112 via one or more dimensions of the acoustic matching layer 252.

In some embodiments, the sensor assembly 251 may include an atraumatic tip, such as the distal tip 108 illustrated in FIG. 1. In some embodiments, the distal tip 108 may include the same material as the acoustic matching layer 252. In some embodiments, the distal tip may include a different material than the acoustic matching layer 252. Additionally or alternatively the distal tip 108 may be formed from one or more layers of materials. The layers may include different materials and/or different configurations (e.g., shape and/or profile, thickness, and/or the like). Further, the distal tip 108 may be arranged to cover the distal surface 272 of the sensing component 112. In some embodiments, the distal tip 108 may also cover a distal end 272 of the housing 280. Moreover, while the distal tip 108 is illustrated as having a domed shape, embodiments are not limited thereto. In this regard, the distal tip 108 may include a flattened profile or any suitable shape. In some embodiments, the entire sensing component 112 may be positioned within (e.g., surrounded by the continuous surface of) the housing 280.

Figure 3A:
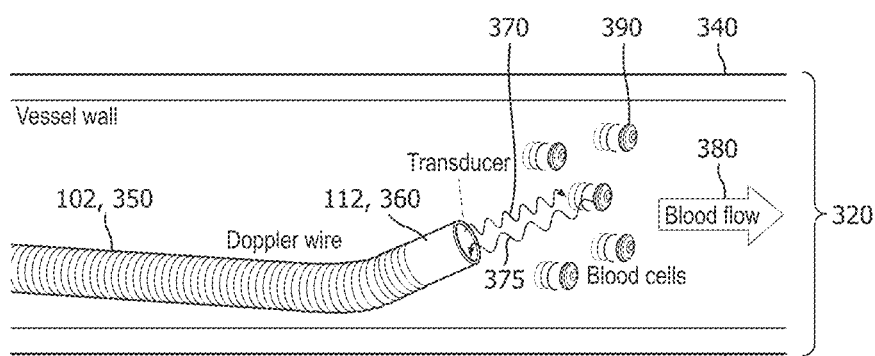
FIG. 3A is a schematic view of an intravascular device during measurement of a flow inside a blood vessel, in accordance with aspects of the present disclosure.

FIG. 3A is a schematic view of intravascular device 102 (e.g., a flow-sensing guidewire 350) during measurement of a flow 380 inside a blood vessel 320 with blood vessel walls 340, in accordance with at least one embodiment of the present disclosure. In the example shown in FIG. 3A, the sensing component 112 (e.g., an ultrasound transducer 360) at the tip is shown to emit ultrasound waves 370 that are backscattered as reflections 375 by flowing cells 390 in the blood and sensed by the transducer 360.

Figure 3B:
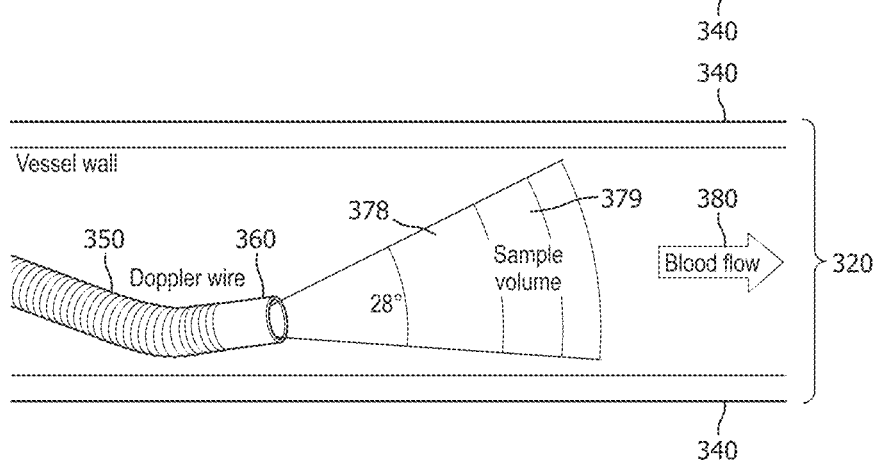
FIG. 3B is a schematic view of an intravascular device during measurement of a flow inside a blood vessel, in accordance with aspects of the present disclosure.

FIG. 3B is a schematic view of intravascular device 102 (e.g., a flow-sensing guidewire 350) during measurement of a flow velocity 380 inside a blood vessel 320 with blood vessel walls 340, in accordance with at least one embodiment of the present disclosure. In the example shown in FIG. 3B, the beam profile or viewing cone 378 of the transducer 360 is schematically shown, along with an example of the sample volume 379 over which the distribution of the flow 380 is measured. This sample volume 379 results from the transducer beam profile or viewing cone 378 as well as the selected measurement distance range, as described below.

Figure 4:
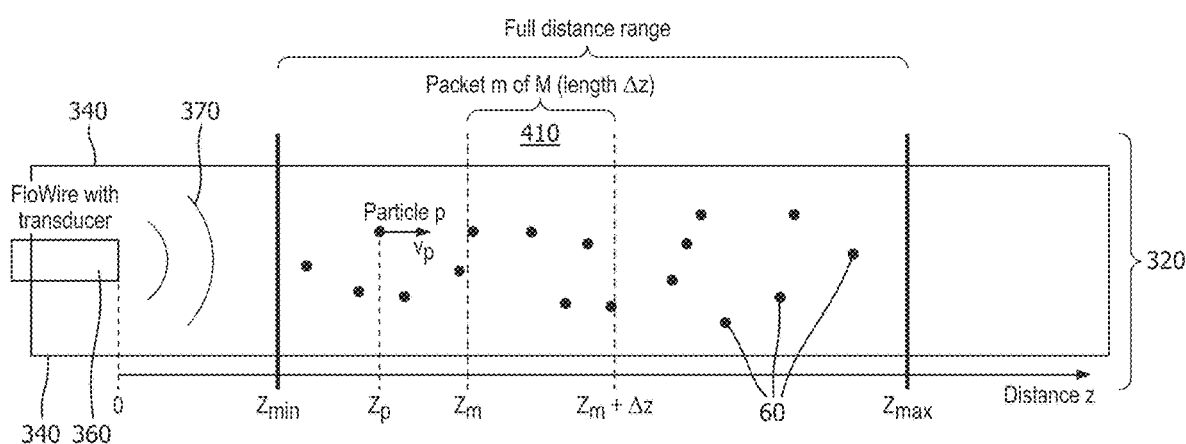
FIG. 4 is a schematic overview of a measurement of intravascular flow using Doppler ultrasound, in accordance with aspects of the present disclosure.

FIG. 4 is a schematic overview of a measurement of intravascular flow using Doppler ultrasound, in accordance with at least one embodiment of the present disclosure. A red blood cell velocity distribution is derived by sending an ultrasound wave or pulse 370 from the transducer 360 into the blood vessel 320. The propagating ultrasound wave or pulse 370 is backscattered by red blood cells 390. The backscattered ultrasound wave is received by the same transducer 360, which converts it into a corresponding electrical signal. In this simplified model, we only consider the axial dimension, Z. At Z=0, the transducer 360 is positioned, and creates ultrasound waves 370 that propagate in the positive Z direction. As the waves travel along the vessel, they are backscattered by cells or particles 390 in the blood. Measurement of low velocity is performed over a distance range $[Z_{min}-Z_{max}]$ in M separate packets 410 (also known as range gates), each covering a distance range of $\Delta Z$ from a minimum range $Z_m$ to a maximum range $Z_m+\Delta Z$. All particles p have a position $Z_p$ and travel along the Z direction with a velocity $V_p$ (which is usually positive but may also be negative).

Figure 5:
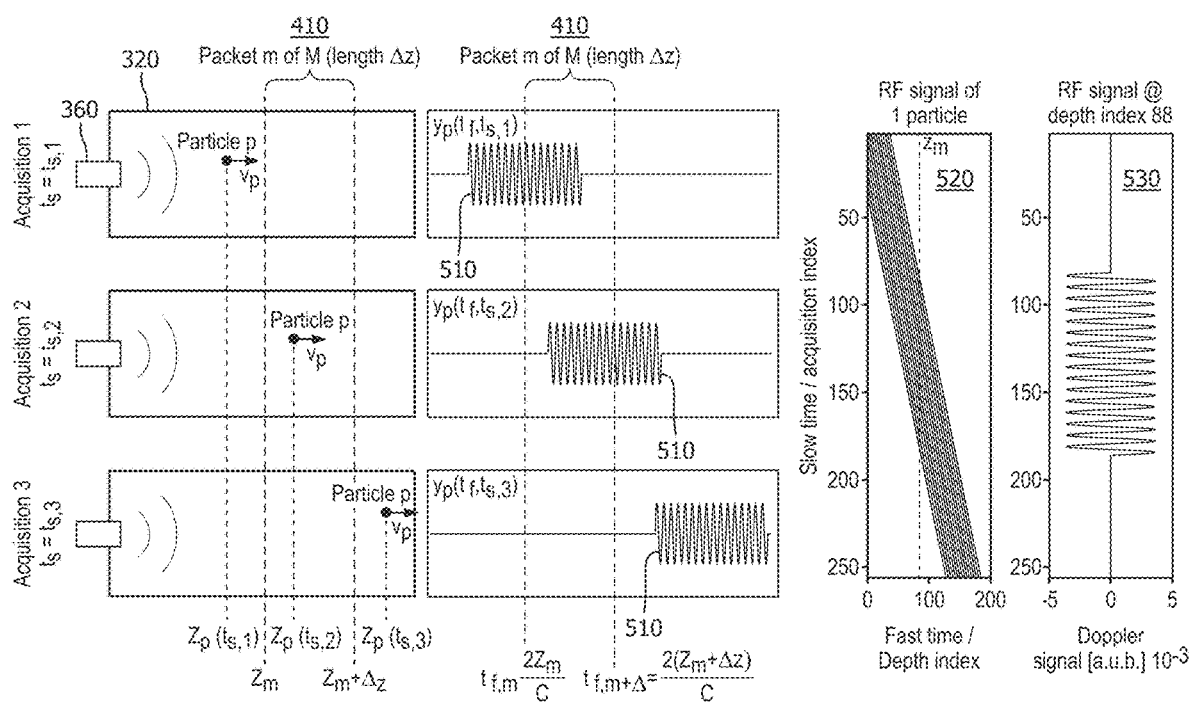
FIG. 5 is a schematic contribution of a flowing particle p within a blood vessel to the Doppler signal matrix, in accordance with aspects of the present disclosure.

FIG. 5 is a schematic contribution of a flowing particle p within a blood vessel 320 to the Doppler signal matrix, in accordance with at least one embodiment of the present disclosure. So far, this disclosure has only considered a single pulse-echo acquisition. However, in a flow-sensing modality, typically an ensemble of subsequent ultrasound pulse-echo acquisitions may be considered. The pulse-echo acquisitions may for example be repeated at a constant pulse repetition interval (PRI). In order to assess velocity, an algorithm considers the displacement of scattering particles between subsequent acquisitions, considering the effect that particles have moved in-between subsequent acquisitions as opposed to moving during a single acquisition. In other words, an algorithm may neglect the 'true' Doppler effect that would cause the frequency $f_c$ of the ultrasound wave in a single pulse-echo acquisition to change as a result of movement of the particles. Doppler analysis may be performed within so-called packets 410, which facilitates the analysis of velocity as a function of the distance Z by a suitable choice of packets with length $\Delta Z$ along the total distance range $[Z_{min}-Z_{max}]$. Graphically, this procedure is displayed in FIG. 5, which shows the pulse-echo acquisitions 510 for a single moving scattering particle as a function of slow time, whereby the slow time $t_s$ is the time covered between subsequent pulse-echo acquisitions. On the left, a particle p is shown in three successive positions as it is moving away from the transducer 360 with velocity $V_p$. In the middle, its pulse-echo contribution 510 to the received signal is shown. In the top case $(Z_p<Z_m)$, the particle is already contributing to the Doppler signal at position $Z_m$ owing to the duration of the transmitted pulse. In the middle case $(Z_m<Z_p<Z_m+\Delta Z)$, the particle has moved further but is still contributing to the Doppler signal within packet m. In the bottom case $(Z_p>Z_m+\Delta Z)$, the particle p has moved completely out of the packet 410 and is no longer contributing to the Doppler signal 520, 530. Further to the right, this particle's contribution is shown as a 2D image with the fast time $t_f$ on the horizontal axis and the slow time $t_s$ on the vertical axis. On the right, the resulting signal 530 along one particular distance/fast-time sample is displayed. The resulting signal 530 is a windowed sinusoid whose frequency (the Doppler frequency) is determined by the velocity of the particle p.

Figure 6:
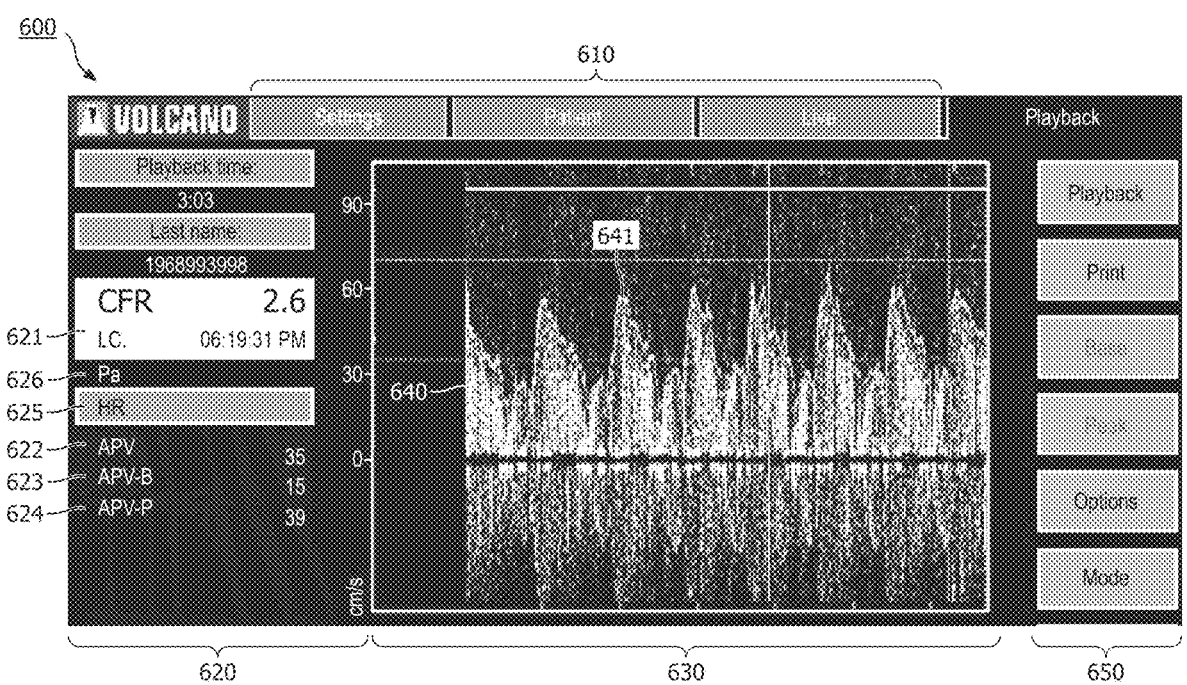
FIG. 6 is an example view of a user interface, in accordance with aspects of the present disclosure.

FIG. 6 is an example workflow screen 600, in accordance with at least one embodiment of the present disclosure. The example workflow screen 600 includes a control tab area 610, a control button area 650, a blood flow statistics area 620, and a waveform display area 630 that contains a waveform 640. Waveform 640 may be representative of a velocity envelope. As shown by the waveform 640, a complete red blood cell velocity distribution is acquired at regular intervals in a certain predetermined packet (volume at a certain distance from the guidewire tip). The flow velocity distribution (in the selected volume) can be graphically shown by plotting the flow velocity along the y-axis at each moment in time (x-axis), as shown by the example velocity waveform 640, and a second waveform 641 showing the instantaneous peak velocity (IPV) of the velocity waveform 640. The brightness or grey scale of the waveforms is indicative of relative incidence of a red blood cell velocity at a particular point in time.

In the example shown in FIG. 6, the blood flow statistics area 620 includes a coronary flow reserve measurement 621, an average peak velocity measurement 622, an average peak velocity baseline measurement 623, an average peak velocity hyperaemia measurement 624, a heart rate measurement 625, and an aortic pressure measurement 626.

For the clinical application the maximum blood cell velocity at each point in time is determined (instantaneous peak velocity=IPV). This IPV value is averaged over a period of time to provide the average peak velocity (APV). For example, the IPV value may be averaged over a single cardiac cycle, two cardiac cycles, three cardiac cycles, four cardiac cycles, five cardiac cycles, or may be averaged over more than five cardiac cycles. The number of cardiac cycles used in calculating the APV may be manually set by a user. This APV is measured during baseline (resting) conditions (APV-B, with B for baseline) as well as during hyperaemia (APV-P, with P for peak). The hyperaemia condition is induced by injecting, e.g., adenosine into the blood. The ratio of the two provides the so-called coronary flow reserve (CFR=APV-P/APV-B). The CFR is a clinically relevant parameter. A CFR value above 2 may be clinically accepted as a healthy coronary flow reserve which does not need treatment. A value below 2 may indicate a need for intervention or follow up. The flow velocity information is shown as a grayscale waveform image 630, 640 in a display format known as a spectral Doppler visualization. The horizontal axis represents time and the vertical axis represents velocity. The grey scale is indicative of relative incidence of a particular velocity measurement at a particular point in time. In practice, as the velocity is measured over a sample volume, a distribution of velocities is measured; each vertical line in the grayscale image 630, 640 represents this distribution, measured in the form of a Doppler spectrum. The spectrum may include an instantaneous peak velocity (IPV), which indicates the maximum velocity at any point in time. This tracing can be automatically determined from the Doppler spectrum and subsequently averaged across one or more cardiac cycles, e.g., between 1 and 5 cardiac cycles, to provide the average peak velocity (APV), which is numerically shown on the left-hand side in the flow statistics area 620. The APV is measured during baseline (resting) condition (APV-B) as well as during hyperaemia (in this case after intra-arterial injection of adenosine, APV-P); the ratio of the two provides the coronary flow reserve (CFR) value. In this case, the example CFR value of 2.6 above an exemplary clinically accepted threshold of 2, which may indicate a sufficiently healthy coronary flow reserve that would generally not require intervention.

FIGS. 7a-11 also provide example workflow screens. The illustrated screens may be displayed as part of a user interface, and aspects of said user interface may be configured to facilitate one or more assessments, procedures, measurements, or the like. For example, the user interface may comprise one or more visualizations that allow a user to quickly review and understand data, including both live and pre-recorded data. In that regard, a user may review and navigate pre-recorded data during live acquisition of new data. Data from multiple data gathering modalities may be displayed concurrently and may be synchronized, e.g., by processing system 306. Though the illustrated screens show certain example modalities, e.g., flow, pressure, electrocardiogram (ECG), the techniques described herein may be applied in the context of other modalities as well. In some embodiments, one or a plurality of the workflow screens in FIGS. 7a-11 is associated with coronary reactivity testing (CRT).

Figure 7A:
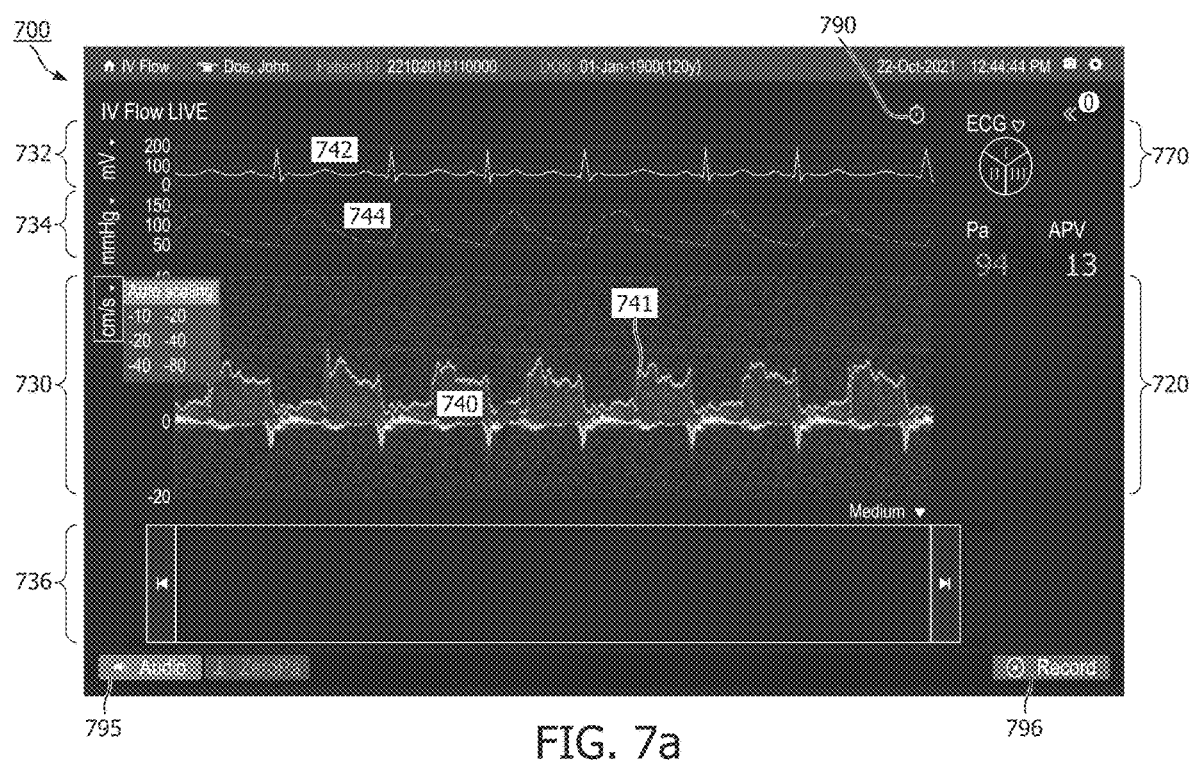
FIG. 7a is an example view of a user interface, in accordance with aspects of the present disclosure.

FIG. 7a is an example workflow screen 700, in accordance with at least one embodiment of the present disclosure. Workflow screen 700 may be displayed in the beginning stages of an assessment or procedure. Workflow screen 700 comprises a plurality of waveform display areas. In that regard, workflow screen 700 comprises waveform display area 730 including a waveform 740 representative of flow data and a trace 741 configured to conspicuously outline the waveform 740, a waveform display area 732 including a waveform 742 representative of ECG data, waveform display area 734 including a waveform 744 representative of pressure data (e.g., blood pressure data), and waveform display area 736 where an interactive trendline may be displayed as discussed in further detail below. Waveform 742 may be an amalgamation of data from multiple ECG leads or may represent data from a single ECG lead. In the case that a single ECG lead is represented, the lead may be selected automatically by processing system 306 or may be selected by a user, e.g., by selecting an option from a menu accessible along the Y-axis of waveform display area 732.

Though four waveform display areas are shown in the example, a greater or lesser number of waveform display areas could be used, e.g., 1, 2, 3, 4, 5, etc. The waveforms displayed may also correspond to different modalities than those discussed above in some cases. As shown, the waveform display areas are independently scaled on their respective y-axes. Independent scaling may advantageously improve visibility of data displayed in the waveform display areas. The processing system 306 may automatically scale the waveform display areas. In that regard, the processing system 306 may determine scale based on an analysis of data to be represented in the waveform display area. Autoscaling may advantageously save a user time, may help to achieve consistent data representation across multiple assessments, and may reduce the likelihood of error on the part of an inexperienced user. Autoscaling may be the default setting or may be specifically activated by a user. In some cases, the user may specify scaling of the waveform display areas.

The workflow display 700 also comprises an audio adjustment button 795. The audio adjustment button 795 can be associated with an audio output device, such as a speaker that is included as part of the system 100 (FIG. 1). The audio output device can be in communication with the processing system 306 in FIG. 1 (e.g., the processor circuit of FIG. 13). In some embodiments, the audio output device can be integrated into the housing of the display 308 and/or the housing of the processing system 306. In some embodiments, the audio output device can be in a separate and/or distinct housing. Certain procedures, e.g., Doppler flow procedures, can be noisy and such noise may be stressful, annoying, or otherwise unpleasant to physicians and patients alike. However, audio is also be helpful during a procedure by, for example, conveying strength and/or cleanliness of a Doppler flow signal. For example, the physician often relies on the characteristic whooshing sound associated with the Doppler flow signal to confirm that the flow sensor is in the correct position and/or orientation with the vessel to collect reliable flow data. The audio may also enable a user to hear the difference between baseline and hyperemic flow. A user, e.g., a physician, can adjust the volume of a procedure by activating the audio adjustment button 795. Such activation may allow the user to reduce the volume of a procedure (including muting the procedure) or increase the volume of the procedure. In that regard, reducing the volume of the procedure advantageously allows a user to limit unwanted noise and thereby reduce a source of stress during the procedure. Increasing the volume of the procedure advantageously allows a user, e.g., a physician, to use audio of the procedure to assess aspects of data acquisition such as the strength and/or cleanliness of a Doppler flow signal as discussed above. Activation of the audio adjustment button 795 may allow the user to manually set the volume of the procedure or may activate an automatic adjustment on the part of the processing system 306.

In some cases, the processing system 306 may automatically adjust procedure volume even in the absence of a user's activation of audio adjustment. In that regard, the processor circuit can automatically change between a louder first volume and a softer second volume (less than the louder first volume). For example, processing system 306 may determine the status of an assessment or procedure and adjust the volume accordingly. In that regard, processing system 306 may lower the volume when in the beginning stages of an assessment or procedure, e.g., before data is being recorded, may lower the volume during an assessment or procedure when it is determined that a user is reviewing previously recorded data, may increase the volume while actively collecting data to be used in calculating clinical parameters, etc.

When flow data is being recorded, the benefits of using procedure audio to assess data acquisition may outweigh the benefits of reducing noise. In some instances, this data can be referenced as first flow data that is obtained while the flow sensor of the intravascular catheter or guidewire is positioned at a data collection location within the vessel. The data collection location can be a longitudinal location within the vessel where the user is intended to collect flow data. It may be advantageous to increase the volume to the louder first volume or maintain the volume at the louder first volume while the first flow data is obtained with the flow sensor is positioned at a data collection location. The sound associated with the first flow data can be output to the audio output device at the louder first volume.

In that regard, it may be advantageous to lower the volume in the beginning stages of a procedure because the benefits of reducing the noise of the procedure may outweigh the benefits of using the audio to assess aspects of data acquisition. Flow data may not even be recorded in the beginning stages of a procedure because, e.g., the intravascular catheter or guidewire is being moved to position the flow sensor at the data collection location within the vessel and/or orient the flow sensor, such as into alignment with the flood flow. It also may be advantageous to lower the volume in interim or ending stages of the procedure, such as when the user is reviewing previously recorded data, or the flow sensor and/or intravascular catheter or guidewire is being repositioned or reoriented to record further data. Flow data obtained by the flow sensor while the intravascular catheter or guidewire is being moved to position the flow sensor and/or while previously collected flow data (e.g., the first flow data described above) is being reviewed by the user can be referred to as second flow data in some embodiments. The sound associated with the second flow data can be output to the audio output device at the softer second volume. In some embodiments, the softer second volume includes the volume level being zero or no audio output being provided to the audio output device.

The processing system 306 (e.g., the processor circuit of FIG. 13) may determine procedure status, e.g., whether the procedure is in the beginning stages, whether data is being recorded, whether the sensor and/or guidewire or catheter is being repositioned, while the user is reviewing previously recorded data, etc. Thereafter, the processor circuit of FIG. 13 can automatically change the sound output on the audio output device between the louder first volume and the softer second volume. For example, the processor can distinguish between the first flow data on the second flow data (e.g., indicative of what stage of the data collection procedure) based on a user input. For example, the system 100 (FIG. 1) can include a user input device in communication with the processing system 306 and that receives a user input. For example, the user input device can be a touchscreen that is part of the display 308, or a separate control console with hard or soft key, a keyboard, a mouse, etc. The user input device can provide a user interface (e.g., a graphical user interface on the touch screen display). For example, the user input can be activating record button 796 to trigger data recording or deactivating the record button 796 to stop data recording. When the user input indicates that the flow data is being recorded (e.g., the first flow data), the processor circuit is configured to change the sound to the louder first volume. When the user input indicates that the flow data is no longer being recorded (e.g., the second flow data), the processor circuit is configured to change the sound to the softer second volume. When the user input indicates previously collected flow data is being reviewed (e.g., one or more user touches on the GUI via the touchscreen to move through previously collected data in time, review other modality data, add bookmarks, etc.), the processor circuit is configured to change the sound to the softer second volume.

In some embodiments, the processor circuit can distinguish between the first flow data and the second flow data (e.g., indicative of what stage of the data collection procedure) based on an analysis of a waveform of the obtained flow data. For example, this waveform can also be displayed on the display 308 (FIG. 1). Analysis of the waveform can include signal processing algorithms, such as pattern recognition. For example, the waveform of the first flow data (e.g., flow data that is obtained to calculate flow metrics such as CFR, APV, etc.) is typically characterized by one or more of periodicity from the heartbeat cycle, similar amplitude/peak values, etc., which can be detected using signal processing algorithms. In response, the processor circuit can change the volume to the louder first volume. In contrast, the waveform associated with the second flow data (e.g., flow data that is obtained while the intravascular catheter or guidewire is being moved, while data is being reviewed, etc.) may be more disorganized, which can be detected using signal processing algorithms. In response, the processor circuit can change the volume to the softer second volume. The disorganization in the waveform can result from the movement of the sensor, because the user is not intentionally positioning and/or orienting the sensor while review prior data, etc.

Workflow screen 700 further comprises timer 790, polar plot 770, and a clinical parameter display area 720. Timer 790 may be activated or deactivated by a user and may start tracking an amount of time elapsed since activation. Timer 790 is advantageously integrated into the user interface such that external timers can be avoided. In some cases, timer 790 may automatically be activated or deactivated in response to a triggering event such as the start of an assessment or procedure, an administration of medication or drugs, a particular occurrence in the data, e.g., an increase over baseline, a decrease under baseline, a waveform peak, a waveform trough, or a calculation exceeding or falling below a threshold, or the like.

Figure 7B:
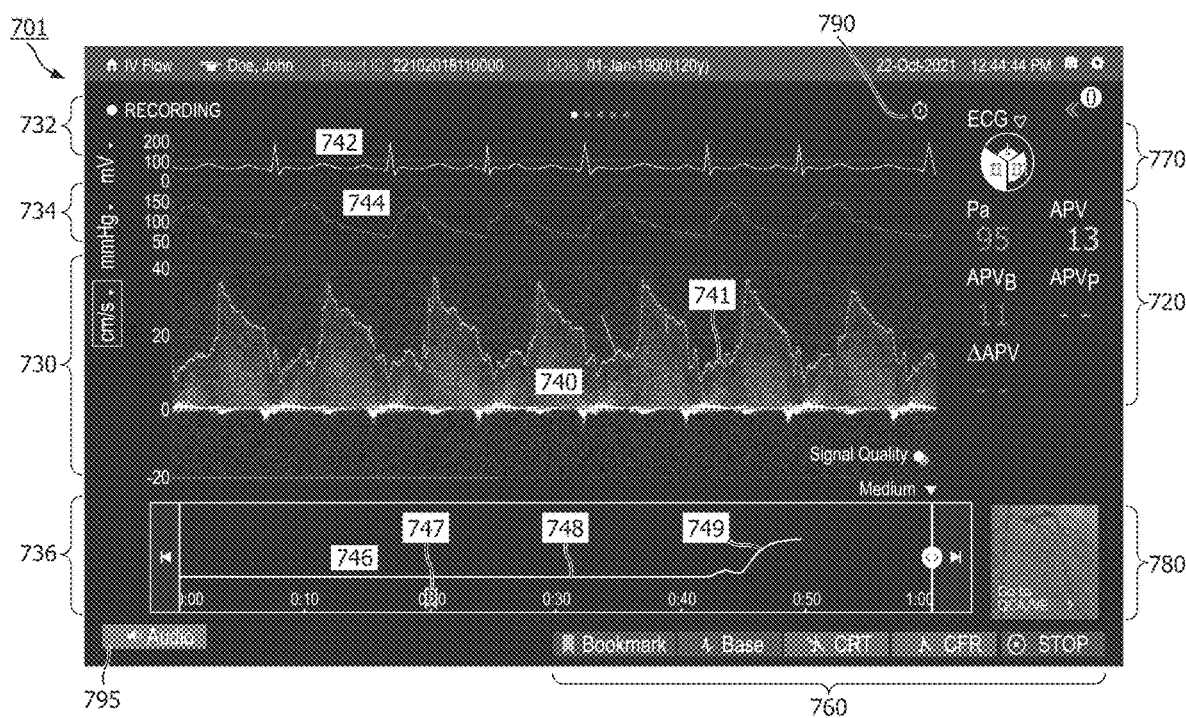
FIG. 7b is an example view of a user interface, in accordance with aspects of the present disclosure.

Polar plot 770 may provide an additional visualization representative of data obtained from one or more of the modalities in use during the assessment or procedure. In the example, polar plot 770 is shown in the context of ECG. In that regard, polar plot 770 is divided into three numbered regions (I, II, and III). Each region may correspond to a separate ECG lead attached to a patient, and data displayed in a given region is representative of data from the lead corresponding to that region. Polar plot 770 improved visibility of conditions detected by ECG. For example, ST elevation can be difficult to see in a waveform. In polar plot 770, ST elevation detected by a lead can be indicated in the region of polar plot 770 corresponding to that lead. The indication may be in the form of a color change, addition of a symbol, addition of a motion, addition of text, or may be in some other form. For example, FIG. 7b shows the polar plot 770 having all the regions colored red, which may be indicative of ST elevation detected by all three ECG leads. Accordingly, by improving the visibility of detected conditions, polar plot 770 advantageously increases the likelihood that the conditions will be promptly recognized by a physician. Such prompt recognition is beneficial because, e.g., in the case of ST elevation, early recognition can reduce the amount of drugs administered to the patient, which in turn reduces the risk of side effects.

Clinical parameter display area 720 can include a plurality of measurements and calculations based on data obtained through one or more data gathering modalities. Clinical parameter display area 720 can include blood flow statistics such as those discussed above with reference to blood flow statistics area 620 and can also include a change in APV.

FIG. 7b is an example workflow screen 701, in accordance with at least one embodiment of the present disclosure. Workflow screen 701 may be displayed after a user activates record button 796 to initiate recording of data. Workflow screen 701 comprises an action panel 760 including various buttons a user may activate to trigger performance of a specified action. In the example, action panel 760 comprises a stop button to stop data recording, a CFR calculation button to trigger CFR calculation, a CRT button to trigger CRT testing, a baseline calculation button to trigger calculation of a baseline, and a bookmark button to trigger addition of a bookmark. Triggering CFR calculation or CRT testing allows the system to search for the highest peak based on the APV value. This peak search may be stopped automatically by the system or may be manually stopped by a user. Clinical parameters displayed in the clinical parameter display area 720 may be calculated in response to activation of one or more of the buttons included in the action panel 760. Activation of a button in the action panel may also prompt the processing system 306 to search for features in the data, where such features may include one or more of an increase over baseline, a decrease under baseline, a peak, a trough, a value exceeding a threshold, or a value falling below a threshold. The particular feature being sought may be indicated on the display.

Also shown in workflow screen 701 is trendline 746 and image 780. Image 780 may be synchronized with one or more of waveforms 742, 744, 740, or trendline 746 such that display of image 780 coincides with a data point gathered or calculated at the same time that image 780 was taken. In the example, image 780 is an angiogram that may be used in CRT. In some cases, image 780 may be taken in response to detection of a feature within one or more of waveforms 742, 744, 740, or trendline 746. For example, reduced blood flow associated with vessel spasm that is induced by acetylcholine in CRT can be visible on one or a plurality of x-ray images. For example, there is reduced flow of contrast agent that has been introduced into the blood vessel when it is under spasm because of the reduced blood flow. Such detectable features may include one or more of the features discussed above. Images from other imaging modalities, e.g., OCT, IVUS, X-Ray, Fluoroscopy, MRI, etc., may also be used in some instances. The image 780 may also act as a link to another application or another mode more particularly suited to viewing and analyzing images.

Trendline 746 can be a plot of the average peak velocity (APV) over time. Trendline 746 may be interactive such that a user can adjust aspects of trendline 746, can navigate to previously recorded data, can navigate from previously recorded data back to live data, and can add bookmarks to the trendline 746. Bookmarks may mark a location of interest. Shown on trendline 746 is bookmark 747. For example, the bookmark 747 can be associated with the baseline value of the APV. The bookmark may be added by a user or may be added automatically by processing system 306. Automatic addition may be triggered based on a shape of the trendline 746, e.g., by detection of a feature within the trendline 746, such as one or more of the features discussed herein. For example, the triggering event can include an increase in the APV (corresponding to the upslope of a peak) by a threshold amount and/or for a threshold amount of time, a decrease in the APV (corresponding to the downslope of a peak and/or a vessel spasm) by a threshold amount and/or for a threshold amount of time, a decrease in the APV following an increase in the APV (e.g., corresponding to a vessel spasm), etc. Multiple bookmarks may be added, and bookmarks may be color coded to distinguish automatically added bookmarks from bookmarks added by a user. The trendline 746 includes a region 748 indicative of the patient's baseline, where the APV is the same. The trendline 746 also includes a region 749 where the APV changes, e.g., because of the influence of a pharmacological agent or medicine (e.g., adenosine, acetylcholine, etc.). In the region 749, the APV velocity is increasing. In general, the trendline can be a plot of values associated with an amount of blood flow (baseline values, increasing values, decreasing values) within the vessel.

In general, the trendline 746 can be a plot of values that are determined based on the flow data obtained by intravascular catheter or guidewire's flow sensor and that are associated with CRT. As the values are plotted in the form of the trendline 746, the progress of one or more aspects of the CRT is represented. The trendline 746 can be progressively generated and displayed (e.g., the values are determined and plotted) to provide a real time or near real time indication of how the CRT is proceeding (e.g., how the patient is responding to a pharmacological agent or medicine, such as acetylcholine, adenosine, etc.). In some embodiments, the progress of the CRT corresponds to a sequence of dosages or doses of the pharmacological agent. The trendline 746 can be representative of how the CRT is proceeding with these dosages (e.g., a patient's physiological response to the sequence of dosages). In some embodiments, the sequence of dosages can include a low dosage (e.g., a first dosage amount), followed by a high dosage (e.g., a second dosage amount different than the first dosage amount), and followed by a low dosage (e.g., the first dosage amount or a third dosage amount different than the first dosage amount). The low dosage(s) can be relatively smaller amount(s) than the high dosage, and the high dosage can be relatively larger amount than the low dosage(s). In some embodiments, the sequence of dosages can include steadily increasing dosages (e.g., multiple dosages that steadily increase from a low dosage to a high dosage). For example, steadily increasing dosages can be linearly increasing or non-linearly increasing. In some embodiments, the sequence of dosages can repeat with the same dosage amounts or different dosage amounts. For example, the sequence of dosages can be repeated with higher dosage amounts for CRT until vessel spasm occurs.

Figure 8:
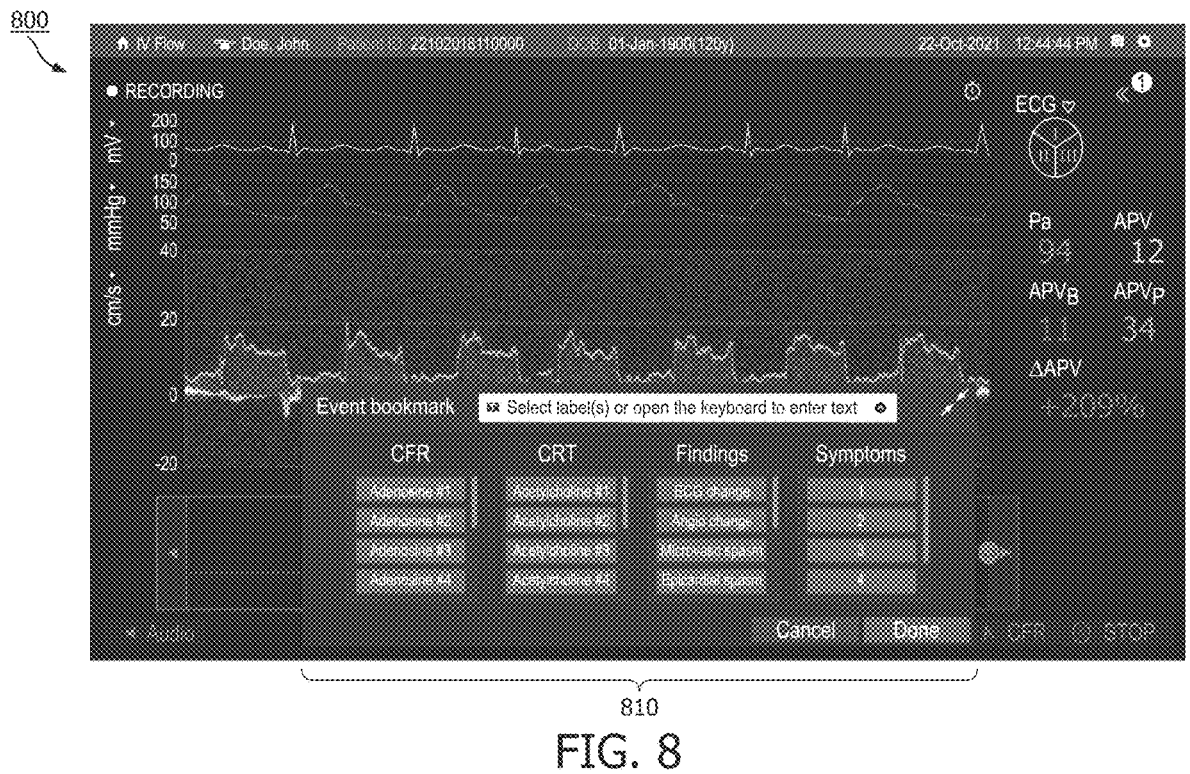
FIG. 8 is an example view of a user interface, in accordance with aspects of the present disclosure.

FIG. 8 is an example workflow screen 800, in accordance with at least one embodiment of the present disclosure. Workflow screen 800 includes bookmark annotation window 810. The bookmarks in the window 810 can be used to annotate the trendline 746. As shown in bookmark annotation window 810, a user may add various annotations, including annotations about CFR measurements, CRT assessments, symptoms, findings, or drugs administered. In some cases, annotations may be automatically added by the processing system 306. Annotations, including automatic annotations, may also be edited or updated by a user. For example, CFR bookmarks can identify when and how many times adenosine was administered, the CRT bookmarks can identify when and how many times acetylcholine was administered, the findings bookmarks can be associated with physiological indications, such as ECG change, angio change, microvascular spasm, and/or epicardial spasm. The symptoms bookmarks can include identifying labels (e.g., numeric, alphabetical, etc.).

Figure 9:
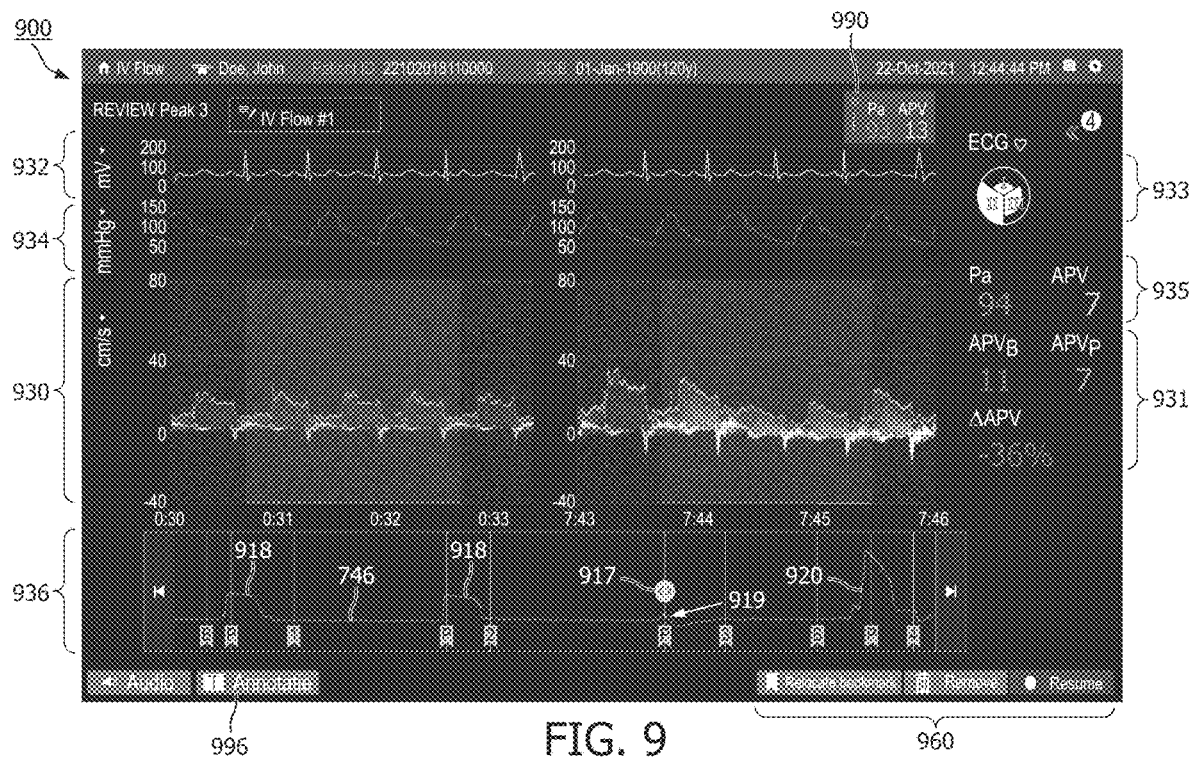
FIG. 9 is an example view of a user interface, in accordance with aspects of the present disclosure.

FIG. 9 is an example workflow screen 900, in accordance with at least one embodiment of the present disclosure. Workflow screen 900 may be displayed when a user goes back to review previously recorded data. The trendline 746 is in FIG. 9 includes multiple features 918, 919, and 920. In some embodiments, at least features 918 and 919 can be associated with CRT. Moving forward in time, starting from the left side of the trendline 746, there are two peaks 918 that are respectively representative of the administration of the first two doses of acetylcholine causing increases in APV. Administration of acetylcholine can be associated with CRT. The second dose of acetylcholine can be larger than the first dose. The feature 919 is representative of a third dose of acetylcholine that is large than the second dose (and the first dose). The third dose of acetylcholine is large enough to induce spasm in the blood vessel, which is a part of the CRT. As shown, the APV increases only slightly and then the APV drops to below the baseline APV (e.g., the value of the trendline 746 between the features 918), which is indicative of the spasm, when there is reduced blood flow through the vessel. To return the patient to baseline, another pharmacological agent (e.g., a vasodilator such as nitroglycerine) can be administered to increase blood flow relative to the decreased blood flow conditions from the spasm. In this example, the user is reviewing "peak 3" (the relatively smaller increase in APV associated with the vessel spasm) on interactive trendline 936. In that regard, the displayed clinical parameters may be those parameters associated with "peak 3." The user may navigate the interactive trendline 936 using by moving scrubber or locator 917 overlaid on the trendline. As scrubber or locator 917 is moved along the interactive trendline 936, numerical clinical parameter values associated with that point are displayed on the right side of screen 900. This advantageously allows a user to quickly navigate through the previously obtained data. In the illustrated embodiment, the numerical values may be associated with the vessel spasm in CRT. The user may also navigate the interactive trendline 936 by selecting a desired bookmark to review. Even though the user is reviewing previously recorded data, live data may continue to be displayed on workflow screen 900 in area 990. Said live data may include one or more current values for the clinical parameters discussed herein.

Bookmarks can also be provided along the trendline 746. For example, a bookmark can be label B for the baseline APV, P for the various peaks associated with acetylcholine or adenosine, and numerical values for physiological findings/indications and/or baseline after respective peaks.

Workflow screen 900 also comprises baseline waveform display areas 930, 932, and 934. The waveforms in these display areas may be based on data obtained under natural conditions, e.g., without administration of hyperemic or other drugs, and may serve as a baseline to which subsequent assessments may be compared. Workflow screen 900 further comprises assessment waveform display areas 931, 933, and 935. The waveforms in these display areas may be based on data obtained under assessment conditions, including after the administration of hyperemic or other drugs. The waveform display areas 931, 933, and 935 can correspond to data associated with the location of the scrubber or locator 917. Workflow screen 900 comprises an action panel 960 featuring options to resume recording, relocate bookmarks, or remove bookmarks. Workflow screen 900 also includes annotation button 996 to allow a user to add annotations.

In some embodiments, the peak 920 can be associated with administration of adenosine. Administration of adenosine can be associated with CFR. In some embodiments, depending on the dosage, the APV can be higher with adenosine than the acetylcholine, as indicated by the higher value of the peak 920 compared to the peaks 918.

Figure 10:
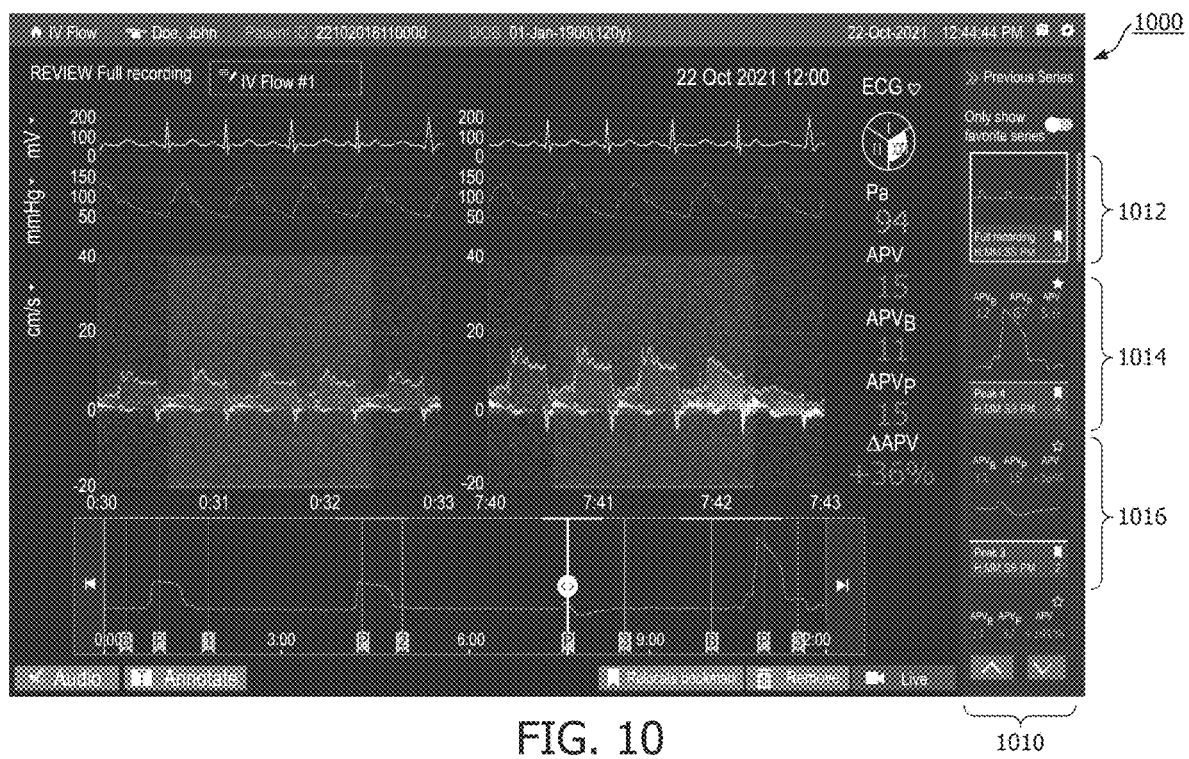
FIG. 10 is an example view of a user interface, in accordance with aspects of the present disclosure.

FIG. 10 is an example workflow screen 1000, in accordance with at least one embodiment of the present disclosure. Workflow screen 1000 may be displayed when a user goes back to review previously recorded data. In this example, the user is reviewing a full data recording. A list of previous measurements may be displayed on workflow screen 1000. The list of previous measurements may be collapsible and may be accessible during from all screens and during all procedures. The list of previous measurements may comprise previous measurements performed during the same procedure.

The list of previous measurements may comprise one or more of pictorial representations, graphical representations, or numerical representations. In that regard, workflow screen 1000 comprises a representation 1012 of a full recording, a representation 1014 of a peak 4 and associated clinical parameters, a representation 1016 of a peak 3 and associated clinical parameters, and a representation 1010 of a plurality of previously obtained clinical parameters.

Figure 11:
FIG. 11 is an example view of a user interface, in accordance with aspects of the present disclosure.

FIG. 11 is an example workflow screen 1100, in accordance with at least one embodiment of the present disclosure. Workflow screen 1100 may be displayed when a user goes back to review previously recorded data. In this example, the user is reviewing a full data recording. A list of previous measurements may be displayed on workflow screen 1100. As discussed above, the list of previous measurements may be collapsible and may be accessible during from all screens and during all procedures and may comprise previous measurements performed during the same procedure. Workflow screen 1100 shows a representation 1110 of a plurality of previous measurements each associated with a respective bookmark. Representation 1110 is an example of a simplified presentation of the previous measurements list. As shown in representation 1110, a timestamp may be displayed alongside the measurements included in the previous measurements list.

Figure 12:
FIG. 12 is an example view of a user interface, in accordance with aspects of the present disclosure.

FIG. 12 is an example workflow screen 1200, in accordance with at least one embodiment of the present disclosure. Workflow screen 1200 may be displayed when a user goes back to review previously recorded data. In this example, the user is reviewing "peak 3." A bookmark 1212 has been added to peak 3 and includes data from within a data window 1219. In that regard, data window 1219 may define a portion of waveform data to be used in calculating one or more clinical parameters. In the example, data window 1219 spans approximately three heartbeats (three cardiac cycles). A user can alter the data window 1219 in various ways. In that regard, a user to include a greater number of beats (cycles) or fewer beats. A user may also select exactly which beats are included, even if the selected beats feature one or more discontinuities. For example, in a set of beats 1 through 5, the user may select all five beats; only one of the beats; any set of four beats; any set of three beats; or any set of two beats. Though the examples are given with respect to heartbeats, the user may define the data window 1219 in other ways as well, including time of measurement, location on a waveform, etc.

The user may also alter a waveform trace and thereby adjust the values that are included within the data window 1219. In that regard, sometimes a waveform includes hallmark signs of noise, interference, or other sources of error. In such cases, a user may adjust a waveform trace so as to smooth out or otherwise alter the waveform so as to omit what appears to be erroneous data.

In addition to the above, a user may also relocate bookmarks, e.g., bookmark 1212, along interactive trendline 1220. In that regard, a user may decide that the data at a given bookmark location is untrustworthy and may be uncomfortable performing alterations to data window 1219 or a waveform trace. In such circumstances, a user may simply use scrubber 1214 to push bookmark 1212 along trendline 1220 until a satisfactory location is found. The processing system 306 may output workflow suggestions, such as suggestion 1210, at any point and on any screen. In the example, suggestion 1210 offers guidance as to how a user can reposition bookmark 1212. Other workflow suggestions may include how to adjust a trace, when to adjust a trace, how to adjust data window 1219, when to adjust a data window, how to annotate a bookmark, how to add a bookmark, when to calculate one or more clinical parameters, when to add a bookmark, how to scale y-axes, how to raise or lower a procedure volume, when to raise or lower a procedure volume, how to interpret a polar plot, or any combination thereof. Workflow suggestions may be pre-programmed, may be added to a user's list of favorites, may be added by experienced users, or may be determined automatically by the processing system 306 based on an analysis of the data or based on a stage of the assessment or procedure.

The ability to perform the adjustments discussed above with reference to FIG. 12 advantageously allows the user to omit obvious sources of error and thereby increase the accuracy of the data and reduce the number of repeated assessments.

Figure 13:
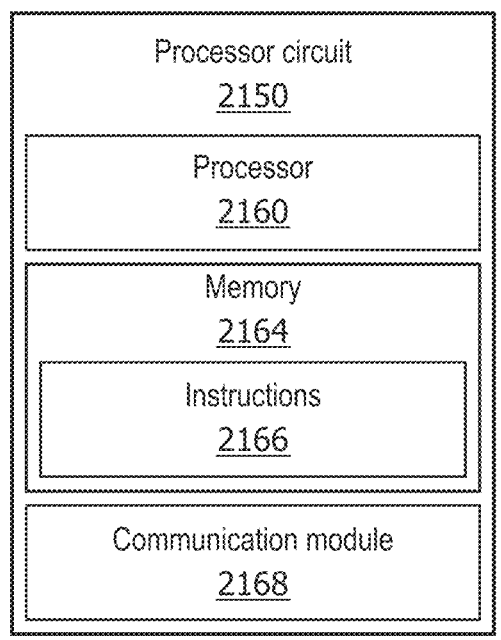
FIG. 13 is a schematic diagram of a processor circuit, in accordance with at least one embodiment of the present disclosure.

FIG. 13 is a schematic diagram of a processor circuit 2150, according to at least one embodiment of the present disclosure. The processor circuit 2150 may be implemented in the intravascular sensing system 100, processing system 306, or other devices or workstations (e.g., third-party workstations, network routers, etc.), or on a cloud processor or other remote processing unit, as necessary to implement the devices, systems, and methods disclosed herein. As shown, the processor circuit 2150 may include a processor 2160, a memory 2164, and a communication module 2168. These elements may be in direct or indirect communication with each other, for example via one or more buses. The processor circuit 2150 may be in communication with one or more of an intravascular device 102, display 308, an ECG device, an angiography device, an X-ray device, an MRI device, an OCT device, an ultrasound device, or other such devices.

The processor 2160 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 2160 may also comprise another hardware device, a firmware device, or any combination thereof configured to perform the operations described herein. The processor 2160 may also be implemented as a combination of computing devices, e.g., a combination of a DSP and a microprocessor, a plurality of microprocessors, one or more microprocessors in conjunction with a DSP core, or any other such configuration.

The memory 2164 may include a cache memory (e.g., a cache memory of the processor 2160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 2164 includes a non-transitory computer-readable medium. The memory 2164 may store instructions 2166. The instructions 2166 may include instructions that, when executed by the processor 2160, cause the processor 2160 to perform the operations described herein. Instructions 2166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 2168 can include any electronic circuitry and/or logic circuitry to facilitate direct or indirect communication of data between the processor circuit 2150, and other processors or devices. In that regard, the communication module 2168 can be an input/output (I/O) device. In some instances, the communication module 2168 facilitates direct or indirect communication between various elements of the processor circuit 2150 and/or the intravascular measurement system 100. The communication module 2168 may communicate within the processor circuit 2150 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

Figure 14:
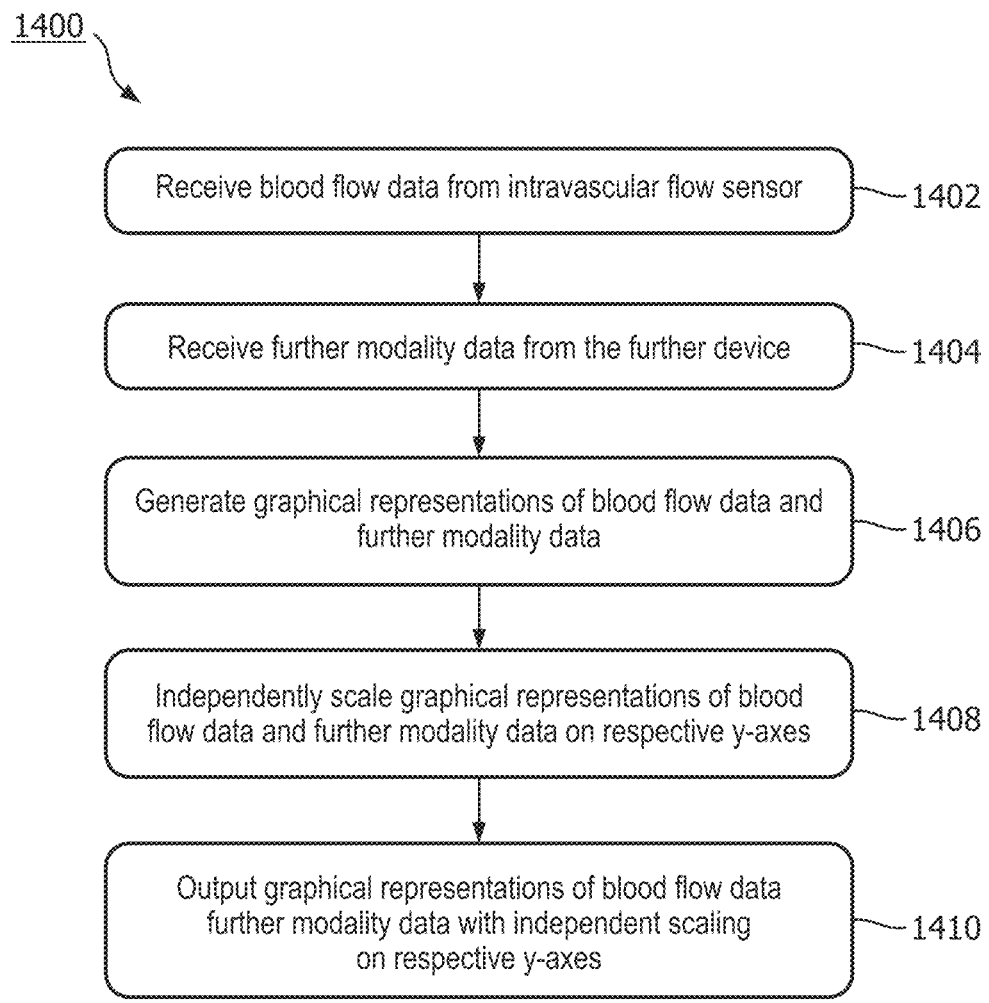
FIG. 14 is a flow diagram of a method for evaluating a blood vessel, in accordance with at least one embodiment of the present disclosure.

FIG. 14 is a flow diagram of a method 1400 of evaluating (e.g., assessing), displaying, and/or controlling (e.g., modifying) assessment of a patient's blood vessel using intravascular blood flow data, according to aspects of the present disclosure. In some embodiments, the method 1400 may be used to control one or more components of the intravascular sensing system 100, as well as additional components. As illustrated, the method 1400 includes a number of enumerated steps, but embodiments of the method 1400 may include additional steps before, after, or in between the enumerated steps. In some embodiments, one or more of the enumerated steps may be omitted, performed in a different order, or performed concurrently. The steps of the method 1400 can be carried out by any suitable component within the system 100 and all steps need not be carried out by the same component. In some embodiments, one or more steps of the method 1400 can be performed by, or at the direction of, a processor circuit of the system 100, including, the processing system 306 (e.g., the processor circuit 2150 (FIG. 13)) or any other component.

At step 1402, the method 1400 includes receiving blood flow data from an intravascular flow sensor. The intravascular flow sensor can be coupled to a distal portion of a guidewire and can obtain the blood flow data while the guidewire is positioned within the blood vessel of a patient. At step 1404, the method 1400 includes receiving further modality data from the further device. For example, the further device can be an intravascular pressure sensor coupled to a distal portion of a guidewire or an ECG device (e.g., ECG electrodes, ECG computing device, etc.). The further modality data can be obtained by the further device and be pressure data, ECG data, etc. At step 1406, the method 1400 includes generating graphical representations of blood flow data and further modality data. For example, the graphical representations can be one or more plots, graphs, and/or curves representative of the values of the blood flow data, pressure data, ECG data, etc. The graphical representations can be generated by signal processing on the signals corresponding to the obtained data (e.g., filtering, amplifying, sampling, compressing, modulating/demodulating, converting (e.g., analog to digital, digital to analog, etc.), mixing, delaying, etc.). At step 1408, the method 1400 includes independently scaling graphical representations of blood flow data and further modality data on respective y-axes. At step 1410, the method 1400 includes outputting graphical representations of blood flow data and further modality data with independent scaling on respective y-axes.

Accordingly, it can be seen that the present disclosure improves the operation of flow-sensing guidewire devices and systems, by permitting the user to understand positioning or alignment problems within a vessel and/or correcting for such problems to construct valid flow measurement data.

The present disclosure may for example be applied with a guidewire that collects intravascular blood flow data only and/or a guidewire that collects intravascular blood flow data only as well as other types of data (e.g., intravascular pressure data). It can also be applied to new flow modalities under the development, both for existing devices and for devices hereinafter developed, either with single transducers or multiple transducers as described above, and comprising either a flow-only sensor or a flow sensor combined with a pressure sensor, or with other sensing modalities. In some embodiments, as part of this development, new patient interface modules (PIMs) may developed that can facilitate the capture of the full raw data signal coming from the flow transducer, to provide raw data for the methods, devices, and systems described herein. The algorithm may include user-viewable features indicative of transducer alignment and/or the quality of flow measurements, or may include automatic changes in the signal strength, waveform, velocity spectrum, or other flow measurement properties without user intervention.

A number of variations are possible on the examples and embodiments described above. For example, the shaped or relative sizes of components may be different than shown herein. The present disclosure may be applied to any flow measurement system incorporating a Doppler flow guidewire. The skew index could also help sonographers orient an external transducer. Other fields of use may include but are not limited to meteorology (e.g., Doppler radar), astronomy (Doppler effect for electromagnetic waves), fluidic, pneumatic, or hydraulic systems (e.g., flow measurement), or any other field of endeavor where there is a spectrum of wavelengths or velocities, and an assessment of the skewness of the spectrum would be helpful in some way.

The logical operations making up the embodiments of the technology described herein are referred to variously as operations, steps, objects, elements, components, or modules. Furthermore, it should be understood that these may be arranged or performed in any order, unless explicitly claimed otherwise or a specific order is inherently necessitated by the claim language. It should further be understood that the described technology may be employed in single-use and multi-use electrical and electronic devices for medical or nonmedical use.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the reinforced multi-filar conductor bundle. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

The above specification, examples and data provide a complete description of the structure and use of exemplary embodiments of the flow measurement system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intravascular blood flow sensing system, comprising:
    an intravascular catheter or guidewire comprising a flow sensor configured to obtain flow data of blood flow within a blood vessel;
    a display; and
    a processor circuit configured for communication with the display and the intravascular catheter or guidewire, wherein the processor circuit is configured to:
    receive the flow data from the intravascular catheter or guidewire;
    determine, based on the flow data, a plurality of values associated with coronary reactivity testing (CRT); and
    output, to the display, a plot of the plurality of values such that the plot is representative of a progress of the CRT.

2. The system of claim 1, wherein the plurality of values comprises a plurality of average peak velocity (APV) values.

3. The system of claim 1, wherein the processor is configured to:
    output, to the display, a locator overlaid on the plot; and
    receive a user input moving the locator along the plot.

4. The system of claim 3, wherein the processor configured to output, to the display, a first graphical representation of the flow data associated with a first position of the locator along the plot.

5. The system of claim 4,
    wherein the plot comprises a baseline,
    wherein the processor is configured to output a second graphical representation of the flow data associated with a second position of the baseline along the plot, wherein the first graphical representation and the second graphical representation are displayed simultaneously.

6. The system of claim 1, wherein the processor is configured to output, to the display, a bookmark along the plot.

7. The system of claim 6, wherein the processor is configured to automatically generate the bookmark.

8. The system of claim 7, wherein the processor is configured to determine a position for the bookmark along the plot based on a shape of the plot.

9. The system of claim 8, wherein the bookmark identifies a peak of the plot.

10. The system of claim 1,
    wherein the plot comprises a plurality of peaks,
    wherein the processor is configured to output, to the display, a list of the plurality of peaks,
    wherein the processor is configured to receive a user input identifying a peak of the plurality of peaks in the list, and
    wherein the processor is configured to output a graphical representation of the flow data associated with identified peak.

* * * * *